US008371851B2

(12) United States Patent  
Smith et al.

(10) Patent No.: US 8,371,851 B2
(45) Date of Patent: Feb. 12, 2013

(54) DENTAL IMPLANT ABUTMENT

(75) Inventors: Jeffrey Smith, Amherst, NY (US); Robert Ganley, Williamsville, NY (US); Dmitri Brodkin, Livingston, NJ (US); Armin Ospelt, Vaduz (LI); Tobias Specht, Ruggell (LI); Hans Peter Foser, Balzers (LI)

(73) Assignee: Ivoclar Vivadent AG, Schaan (LI)

( * ) Notice: Subject to any disclaimer, the term of this patent is extended or adjusted under 35 U.S.C. 154(b) by 226 days.

(21) Appl. No.: 12/027,657

(22) Filed: Feb. 7, 2008

(65) Prior Publication Data

US 2008/0274440 A1    Nov. 6, 2008

Related U.S. Application Data

(63) Continuation-in-part of application No. 10/799,513, filed on Mar. 12, 2004, now abandoned.

(51) Int. Cl.
*A61C 8/00*    (2006.01)

(52) U.S. Cl. ...................................... 433/173; 433/203.1

(58) Field of Classification Search .......... 433/172–175, 433/199.1, 201.1, 202.1, 203.1; 700/97–98, 700/118; 264/16–20; 428/542.8
See application file for complete search history.

(56) References Cited

U.S. PATENT DOCUMENTS

| | | | |
|---|---|---|---|
| 4,970,032 A | 11/1990 | Rotsaert | |
| 4,988,298 A | 1/1991 | Lazzara et al. | |
| 5,151,044 A * | 9/1992 | Rotsaert | 433/229 |
| 5,261,815 A | 11/1993 | Pozzi | |
| 5,685,714 A | 11/1997 | Beaty et al. | |
| 5,989,029 A | 11/1999 | Osorio et al. | |
| 6,030,209 A | 2/2000 | Panzera et al. | |
| 6,039,568 A | 3/2000 | Hinds | |
| 6,139,318 A | 10/2000 | Foser | |
| 6,231,342 B1 | 5/2001 | Osorio et al. | |
| 6,250,922 B1 | 6/2001 | Bassett et al. | |
| 6,368,108 B1 | 4/2002 | Locante et al. | |
| 6,379,593 B1 | 4/2002 | Datzmann et al. | |
| 6,380,113 B1 | 4/2002 | Kim et al. | |
| 6,497,573 B2 | 12/2002 | Wagner et al. | |
| 6,755,651 B2 | 6/2004 | Brodbeck | |
| 7,086,863 B2 * | 8/2006 | Van der Zel | 433/223 |
| 7,179,089 B2 | 2/2007 | Sims et al. | |
| 7,494,539 B2 | 2/2009 | Ikushima et al. | |
| 2005/0084819 A1 * | 4/2005 | Sims et al. | 433/173 |
| 2005/0106534 A1 * | 5/2005 | Gahlert | 433/173 |
| 2006/0084035 A1 * | 4/2006 | Volz | 433/173 |

(Continued)

FOREIGN PATENT DOCUMENTS

EP    0455854 A1 * 11/1991
WO    WO02/09612 A1 * 2/2002

(Continued)

OTHER PUBLICATIONS

"Estenia C&B: Implant Superstructure". Kuraray Medical Inc.*

(Continued)

*Primary Examiner* — Cris L Rodriguez
*Assistant Examiner* — Edward Moran
(74) *Attorney, Agent, or Firm* — Ann M. Knab; Thad McMurray

(57) ABSTRACT

A dental implant abutment for attaching a dental prosthesis within a patient's mouth. The abutment is a single unit structure fabricated of a ceramic material, multicolored throughout to match the color of the dental prosthesis, the surrounding dentition and the surrounding gingival tissue.

40 Claims, 4 Drawing Sheets

U.S. PATENT DOCUMENTS

| | | | |
|---|---|---|---|
| 2006/0246399 A1* | 11/2006 | Ehrl | 433/201.1 |
| 2007/0042889 A1 | 2/2007 | Apel et al. | |
| 2007/0056467 A1* | 3/2007 | Panzera | 106/35 |
| 2007/0292597 A1 | 12/2007 | Ritzberger et al. | |

FOREIGN PATENT DOCUMENTS

| | | | |
|---|---|---|---|
| WO | WO/2006/031096 | * | 3/2006 |

OTHER PUBLICATIONS

"Estenia C&B: Implant Superstructure". Kuraray Medical Inc. 2005.*

Denry et al., "State of the art of zirconia for dental applications," Dental Materials, 24 (2008) 299-307.

Sailer et al., "Five-year Clinical Results of Zirconia Frameworks," Int J Prosthodont., Jul.-Aug. 2007, 20(4), 383-388.

http://dictionary.reference.com/browse/monolithic; Nov. 22, 2010.

http://www.answers.com/topic/monolith; Nov. 23, 2010.

R. Cominotti, "Near net shape technology: An innovative opportunity for the automotive industry," Journal Robotics and Computer-Integrated Manufacturing, vol. 24, Issue 6, 2008, Abstract.

* cited by examiner

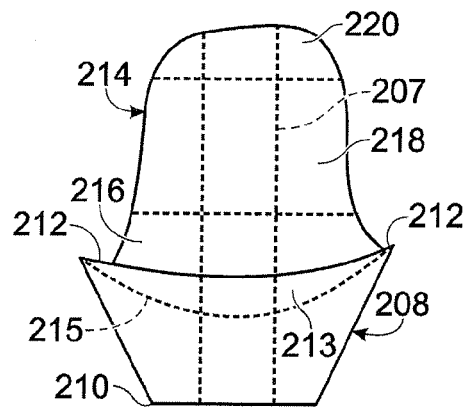
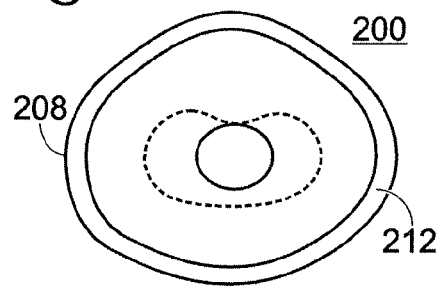
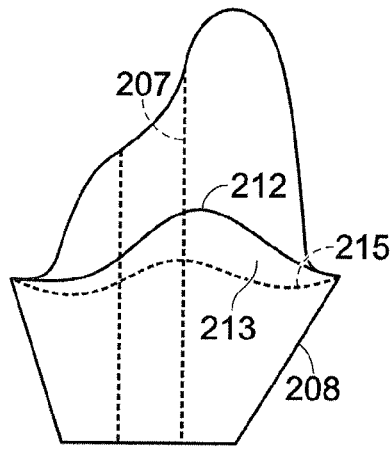
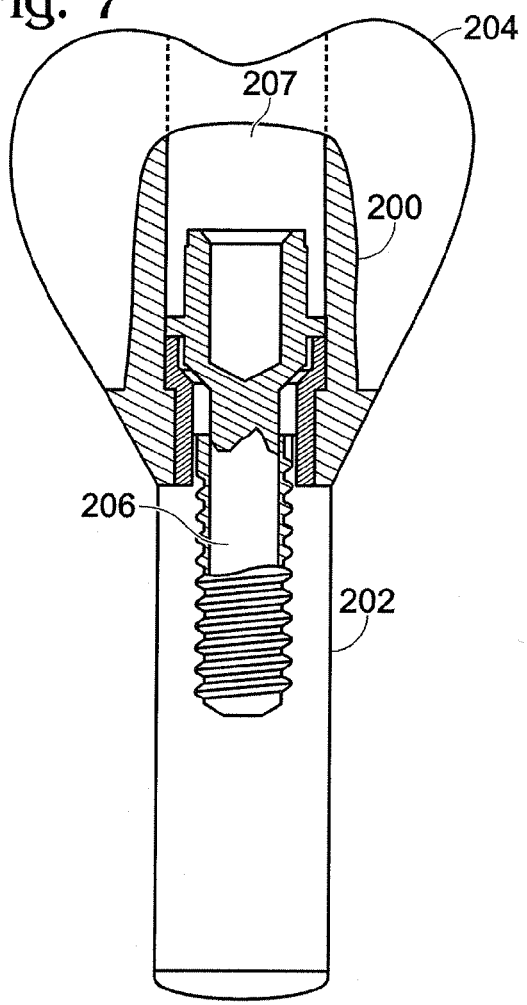

DENTAL IMPLANT ABUTMENT

REFERENCE TO RELATED APPLICATIONS

This application is a continuation-in-part of U.S. application Ser. No. 10/799,513, filed Mar. 12, 2004, now abandoned, which is hereby incorporated by reference.

BACKGROUND

The present invention relates generally to restorative dentistry. More specifically, the invention relates to an implant abutment for dental restorations.

Restorative dentistry has made significant advances in the use of dental implants to support dental restorations intended to permanently replace natural teeth. Dental implants provide an alternative to removable dentures, fixed partial dentures, and single-tooth restorations.

In a jawbone anchored dental restoration, an implant of known design is surgically implanted into a patient's jawbone, leaving a gingival surface exposed. A support post, commonly referred to as an abutment, is then firmly fixed to the exposed surface of the implant. A dental prosthesis is secured to the abutment by means of a screw extending through a bore in the prosthesis and into a threaded bore in the abutment (screw retained) or via conventional cementation techniques (cement retained).

As described, for example, in U.S. Pat. No. 4,988,298 to Lazzara et al., the entire content of which is incorporated herein by reference, and as shown in FIG. 1, a dental implant restoration system 10 generally includes a dental implant 14, a support post or abutment 16, and a prosthesis 12. The implant is typically made from a biocompatible material such as titanium or titanium alloy, and is embedded into the jawbone leaving a gingival surface 22 flush or nearly flush with the gingival surface A-A of the jawbone. This gingival end includes an internally-threaded recess 24 and a multi-sided male projection for abutting with the abutment 16. The abutment 16 is securely attached to the lower or gingival end of the prosthesis 12 and functions to provide a rigid interconnection between the implant 14 and the prosthesis 12.

A passageway extends through the abutment 16 and provides a recess at the transgingival portion for engaging the projection of the implant. A screw 26 abuts against a shoulder 28 of the abutment and engages the threaded recess 24 of the implant to force a precision formed abutment surface 29 into seated contact with the gingival surface of the implant. The prosthesis 12 is fabricated around the upper portion of the abutment and may be connected to the abutment via screw 26 or cement. The prosthesis is colored to match the surrounding dentition.

Typically, the abutment is made of metal, such as titanium, and the prosthesis is fabricated from ceramic, a ceramic-based material such as porcelain, or a polymeric resin material. An entirely metallic abutment however, can be visible through the prosthesis, resulting in a dark, central rod-like shadow, particularly when exposed to bright light, which makes the prosthesis somewhat unattractive since it is distinguishable from a natural tooth. Various methods for preventing or masking the appearance of the shadow are known in the art.

One attempt to solve the attractiveness problem involves making a support post entirely of tooth-colored ceramic material. This approach allows direct surface bonding by interaction of a porcelain coping and/or prosthesis to the support post, resulting in a secure and almost seamless bond between the prosthesis and support post. While presenting an attractive alternative to the use of a titanium support post, the proposed solution presents a number of problems.

Ceramic materials generally have a much greater hardness than titanium. When an all-ceramic support post is used, inevitable rocking of the support post due to, for example, chewing, causes a high stress interaction between the metal implant and the ceramic material of the post. Since a ceramic support post is of greater hardness than a titanium implant, it can and does cause damage to the implant. If sufficient damage is caused, eventual surgical intervention is required to remove and replace the titanium implant. In addition, ceramic material is typically not radiopaque, and when using conventional x-ray imaging to examine the juncture between the abutment and the titanium implant, the interface between the two elements is not readily viewable and adequate examination cannot be conducted. Moreover, fracture of the all-ceramic post is also a consideration.

Recognizing the benefits of a metallic support, U.S. Pat. No. 5,685,714 to Beaty et al. describes an abutment having two distinct sections. As seen in FIG. 2, abutment 12 includes an inner section, or core 36, made from titanium or a titanium alloy and an outer section, or cuff 34, made from ceramic, typically aluminum oxide. The metallic core 36 provides the necessary strength to the abutment and provides a framework for connecting prosthesis 38 to implant 40. The ceramic cuff 34 preferably surrounds the entire exterior surface of the core 36, and shields the shadow of the metallic core 36 through the prosthesis 38. PureForm™ (Centerpulse Dental Inc., Carlsbad, Calif.), for example, is a tooth-shaped abutment composed of a titanium core and a ceramic cuff made of an alumina/zirconia blend. Screw-retained alumina or zirconia/alumina based abutments are available under the trademarks Bio-Cera™ (Bio-Lok International, Inc., Deerfield Beach, Fla.), CerAdapt™ (Nobel Biocare™ AB, Goteborg, SE) and ZiReal™ Post (Implant Innovations, Inc., Wilmington, Del.).

U.S. Pat. No. 6,497,573 to Wagner et al. describes a three part dental abutment that includes a shield between a metallic core and a polymeric cuff. The shield is preferably formed of an opaque material, such as a mixture of several mono and dimethacrylates, and may include various pigments to provide a variety of colors to best shield or mask any grayish or metallic color of the core.

U.S. Pat. No. 7,179,089 is directed to a two-part abutment having an upper section fabricated of a metal, zirconia or alumina cylinder and a shoulder attached to the cylinder and fabricated of a hybrid ceramic material, whereby a pigment may be added to the hybrid ceramic material to match the color of the patient's gum tissue.

Each of the aforementioned devices however, have certain drawbacks. The three part system is inherently more costly, both in time and materials. The two-part system of U.S. Pat. No. 7,179,089 requires the attachment of the cylinder to the shoulder component. Moreover, the two part systems, while effectively masking the shadow of the metallic core, result in the requirement for additional time and expertise in the fabrication of the prosthesis. When utilizing an entirely metallic abutment, the technician simply acknowledged the resulting appearance of the shadow and fabricated a prosthesis that matched the surrounding dentition. With the addition of a cuff component, however, the color of the cuff and the color of the prosthesis combine to create the color of the final restoration, and the technician must therefore take the color of the abutment into consideration when fabricating the prosthesis.

This is particularly important when the prosthesis is fabricated of ceramic. Since most ceramic restorations have inherent translucency, it is incumbent that the abutment be shaded so that it complements the desired shade of the restoration.

This process is similar to determining the shade of a natural tooth prior to the fabrication of an all ceramic crown. In that case, it is recognized that the underlying natural tooth or "stump" will influence the shade of the final restoration.

U.S. Pat. Nos. 6,231,342 and 5,989,029 are directed to customized abutments and are hereby incorporated by reference. The abutments are customized by taking a series of measurements at the tooth site and fabricating an abutment based on the measurements. Although the abutments, are customized single-unit structures, there are no color and shade considerations.

Conventional abutments, such as PureForm™ Ceramic Coping (Centerpulse Dental Inc., Carlsbad, Calif.), Bio-Cera™ (Bio-Lock International, Inc., Deerfield Beach, Fla.), CerAdapt™ (Nobel Biocare™ AB, Goteborg, SE) and ZiReal™ (Implant Innovations, Inc., Wilmington, Del.), are typically available in one standard color chosen by the manufacturer, regardless of the material they are made from. Thus, an "exact match" between the abutment and prosthesis is not achieved. CerAdapt™ abutments for example, are available in Vita-Shade™ A-3 (Vita Shade™ Guide, Vident, Brea, Calif.).

SUMMARY OF THE INVENTION

In one embodiment, the present invention provides an aesthetic implant abutment for attaching a restorative dental prosthesis within a patient's mouth. In accordance with the invention, the implant abutment includes a core and a cuff surrounding the core, wherein the cuff is colored to match the color of the prosthesis.

In various embodiments, the core is fabricated from metal, such as titanium or a titanium alloy, and the cuff and prosthesis are fabricated from a ceramic or polymeric material. In a preferred embodiment, both the cuff and prosthesis are formed of ceramic.

The invention further provides a dental implant restoration system that includes an implant, a dental abutment having a core and a cuff surrounding the core fixed to the implant, and a dental prosthesis fixed to the abutment, wherein the abutment cuff is colored to match the color of the prosthesis.

The invention also provides a method of fabricating a dental implant restoration that includes, fixing an implant within a patient's mouth; fixing a dental abutment having a core and a cuff surrounding the core, to the implant; and fixing a dental prosthesis to the abutment, wherein the abutment cuff is colored to match the color of the prosthesis.

In yet another embodiment, a single unit abutment is fabricated of a ceramic material, shaded to match the color of the dental prosthesis, and/or the surrounding dentition and the surrounding gingival tissue. The abutment is anatomically shaped and shaded to match the near net shape and shade of the prosthesis that is attached thereto. As the abutment gets closer to the net shape and becomes more naturally shaded, it obviates the need for a restoration on top and becomes the restoration itself. Additionally, the abutment is shaded to match the color of the surrounding dentition and gingival tissue.

BRIEF DESCRIPTION OF DRAWINGS

FIG. 4 is a perspective view of the facial side of the abutment according to an embodiment of the present invention.

FIG. 5 is a perspective view of the lateral side of the abutment of FIG. 4.

FIG. 6 is a perspective view of the top side of the abutment of FIG. 4.

FIG. 7 is a partial cross-sectional view of a dental implant system according to another embodiment of the present invention.

DETAILED DESCRIPTION OF THE INVENTION

Figure 1:
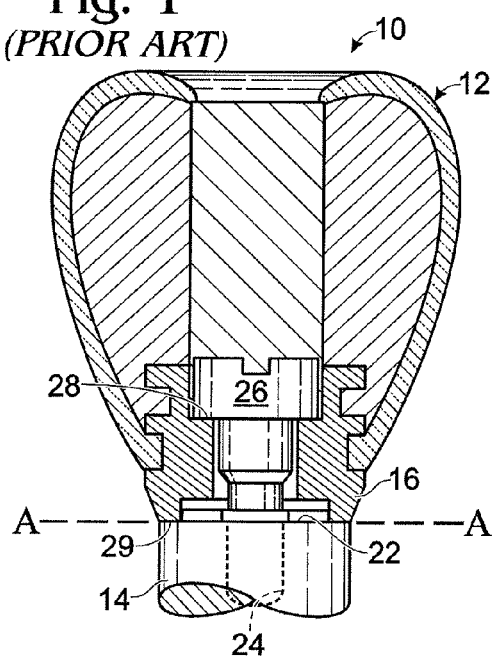
FIG. 1 is a partial cross-sectional view of a prior art dental abutment fixed within a dental implant restoration system.
Figure 2:
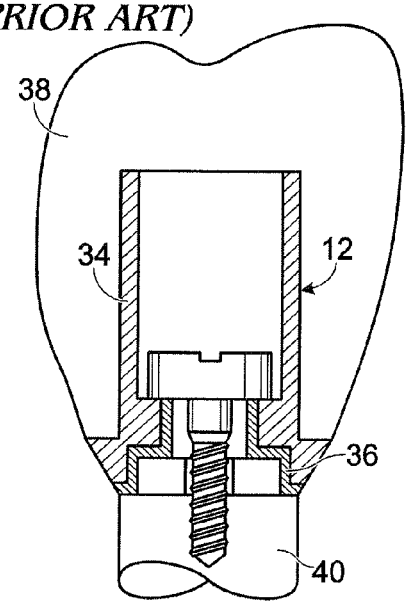
FIG. 2 is a partial cross-sectional view of a prior art dental abutment fixed within a dental implant restoration system.
Figure 3:
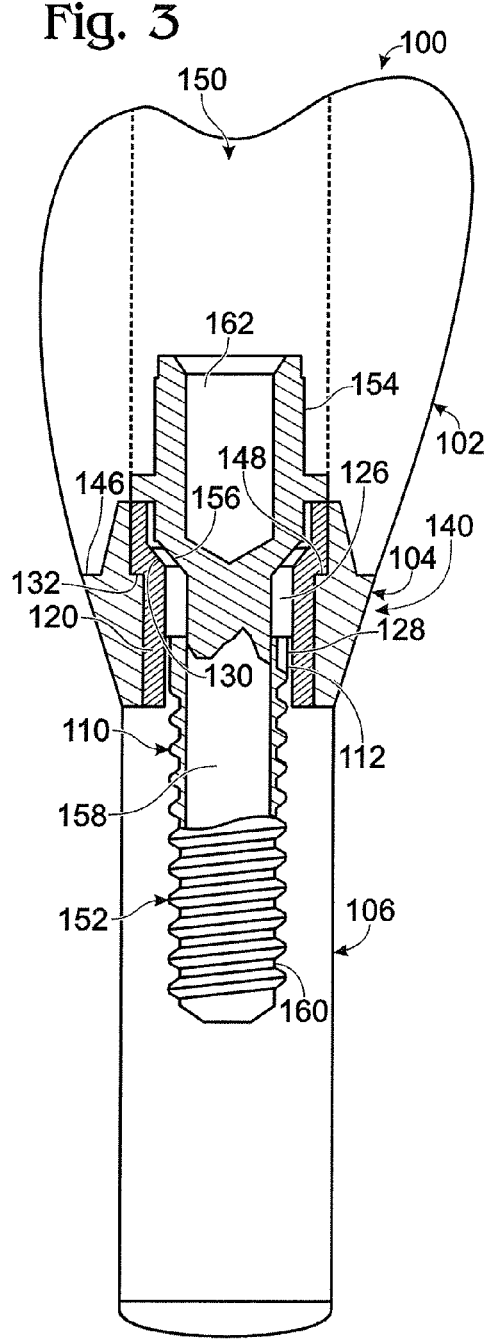
FIG. 3 is a partial cross-sectional view of a dental restorative system according to one embodiment of the present invention.

FIG. 3 shows a dental restorative system 100 that includes a prosthesis 102, an abutment 104, and an implant 106. The abutment and prosthesis are attached together and connected to the implant as illustrated.

Implant 106 has a coronal or gingival end with a threaded bore 110 and a male engaging feature 112 extending upwardly. The coronal end extends downwardly along a cylindrical body to a distal end. The male engaging feature 112 connects to the abutment and may be a plurality of upwardly extending tines, a polygon, or other type feature known to those skilled in the art. Alternatively, the implant may have female engaging features that correspond with male projections on the abutment core. The implant may be any one of various implants known in the art, such as those manufactured by Sulzer Calcitek Inc. (Carlsbad, Calif.).

Abutment 104 has two different and distinct sections preferably formed from two different materials. Core section 120 has a cylindrical configuration and extends from a top portion to a bottom portion. A passageway 126 extends centrally through the core. The bottom portion abuts against the coronal end of implant 106. Abutment 104 may be provided with a female engaging feature 128 that engages with the male engaging feature 112 to provide an anti-rotational connection between the abutment and implant. The engaging features would have matching configurations to provide the noted anti-rotational connection. Numerous configurations of engaging features known to those skilled in the art (such as Spline® tines, octagons, and other polygons) may be used.

Core 120 typically includes a shoulder 130 located along the interior of the passageway 126 at the top portion. A corresponding ledge 132 is formed along the exterior surface adjacent shoulder 130. Preferably, the core is made from a biocompatible metal, such as titanium or its alloys. The metallic core provides strength to the abutment and a framework for connecting the prosthesis to the implant.

An abutment cuff section 140 connects to the exterior surface of the core 120 and, preferably, surrounds the entire exterior surface. The cuff has a somewhat cylindrical configuration and extends from an upper portion to a lower portion.

The cuff can be shaped around the core to have various configurations, such as a cylindrical or elliptical configuration or an anatomical shape that resembles the cross section of a natural tooth.

As shown in FIG. 3, the cuff 140 tapers outwardly and upwardly away from the coronal end of the implant 106 and forms a frusto-conical shape. This tapering continues to a ledge 146 and then transitions to taper inwardly at the upper portion of the cuff 140. A shoulder 148 is located along the inner surface. This shoulder 148 fits with the mating ledge 132 on the exterior of the core.

The prosthesis 102 is shaped as a natural tooth and includes a passageway 150 that aligns with the passageway 126 of the abutment. A screw 152 passes into these passageways until a head 154 of the screw abuts against the top portion of the core. As shown, the lower portion of the head includes a taper 156 that abuts against the shoulder 130 along the interior of the core. The screw includes a shank 158 extending from the head. This shank has a threaded portion 160 that fits into the coronal end of the implant to engage corresponding threads in threaded bore 110. The screw holds the abutment and attached prosthesis to the implant. The head 154 also includes a recess 162. The recess may be provided to engage a tool (not shown) for tightening and loosening the screw or provided to threadably engage another screw (not shown) to secure the prosthesis.

In accordance with one embodiment of the invention, the color of the abutment cuff 140 matches the color of the prosthesis 102. While the cuff 140 and the prosthesis 102 are preferably made from a ceramic material, such as the zirconia/alumina composite described in U.S. Pat. No. 6,380,113 to Kim et al., various polymers and polymer combinations such as acrylic polymers; fiber, glass, silica, and alumina reinforced polymers; thermosetting and photosensitive polymers; vinylesters; and epoxy type materials, may also be used. Suitable polymers include Sculpture™ or FibreKor™ of Jeneric/Pentron, Inc. (Wallingford, Conn.) and Targis™ or Vectris™ of Ivoclar Vivadent, Inc. (Schaan, LI).

In the context of the present invention, "matching" the color of the abutment cuff to the color of the prosthesis means choosing a color for the abutment cuff that is most similar to the color of the prosthesis. Generally, a restoration is fabricated in more than one color shade, typically with a darker shade at the gingival surface and a brighter shade at the top. However, the abutment color is selected to match the overall color of the prosthesis, especially at the interface of the abutment 140 and the restoration 104.

Several methods are known in the art for determining the color of a dental restoration. Most commonly used is a dental shade guide, which generally has a base supporting a plurality of tabs or other indicia, each of which corresponds to a different color. The colors of the tabs/indicia represent a range of standard tooth colors. U.S. Pat. No. 6,139,318 to Foser, for example, the entire content of which is incorporated herein by reference, describes a particularly useful color key for selecting a proper color for a dental restoration. The color key includes a number of detachable, tooth sample elements that are formed of the same materials and colored in the same manner, as the dental restoration. In addition, the tooth sample elements include a first surface having a texture and curvature that matches a natural tooth, and a second surface that is smooth and flat. The first surface provides the possibility to test the impression the identically produced restoration will have in the same location, while the second surface provides an improved evaluation of color only, as it can be positioned more easily within the patient's mouth for comparison with surrounding dentition.

Other, commercially available dental shade guides include, for example, Chromoscop™ (Ivoclar Vivadent, Inc., Schaan, LI); Vitapan Classical™ (Vita-Lumin™ Vacuum Shade Guide) and Vitapan 3-D Master™ (Vident, Brea, Calif.); and Bioform™ and TruMatch™ (Dentsply International, Inc., Milford, Del.).

Once the color of the prosthesis has been determined, an abutment having a cuff that most similarly matches that color is used in the implant restoration. Depending upon the dental shade guide system being used, a series of colored abutments, specific for that system, would be available to chose from.

The principles of the present invention thus provide several advantages over conventional dental implant restoration systems. The invention simplifies the restoration process, in that the fabrication of the prosthesis no longer has to take the color of the abutment into consideration. The abutment includes a cuff matching the color chosen for the prosthesis. Therefore, the interface between the abutment and the restoration is aesthetically enhanced and visually less detectable. In contrast, in accordance with the prior art, the color of the restoration was determined by the combination of the colors of the abutment and the prosthesis. Typically, the technician creating the restoration would obtain a standard abutment and then determine a color for the prosthesis that, when combined with the color of the abutment, would result in the desired color for the final restoration.

By utilizing an abutment having the same color as the prosthesis, the final restoration has a greater depth, providing a much more natural appearance. Just as the "stump" of a damaged tooth provides a natural-colored framework for the reconstruction of the tooth, the abutment of the present invention provides a natural-colored framework for the fabrication of a prosthesis.

In some instances, the restoration may include a layer of dental cement between the abutment and the prosthesis. Prior to the present invention, the practitioner would choose a cement having a color that would properly combine with the colors of the abutment and the prosthesis, to obtain the desired color for the final restoration. With the present invention, however, because the abutment matches the color of the prosthesis, no additional determinations are required, and a clear cement may be used.

In a typical jawbone anchored dental restoration, after the implant system has been fixed within the patient's mouth, the gum is restored around the system, such that it extends above the lower surface of the prosthesis. With normal aging however, it is not uncommon that the gum line will recede, exposing the lower surface of the prosthesis, as well as a portion of the abutment. With prior art abutments, this could cause an unsightly, unnatural appearance. In accordance with the present invention, however, as the color of the prosthesis and the abutment cuff are matched, the appearance of the abutment is not noticeable even if exposed, and the implant restoration blends naturally with the surrounding dentition.

FIGS. 4 through 6 show another embodiment of an abutment 200 of the present invention. Abutment 200 is a monolithic or single-unit structure, which can be anchored to an implant 202 shown in FIG. 7. A dental prosthesis, such as a crown 204 shown in FIG. 7, is positioned over abutment 200, which is connected to implant 202 with an attachment screw 206 through bore 207 in abutment 200. In such design, the abutment has a female connection component and the implant body has a male connection component. It should be mentioned that the means of attachment of abutment 200 to an implant is not limited to an exterior anti-rotational connection as depicted in FIG. 3. Other modes and methods of attachment may be used, including but not limited to, internal connection components. The abutments herein may be adapted to connect to any type of implant.

Abutment 200 is a single-unit structure fabricated of a ceramic material. As shown in FIGS. 4 through 7, abutment 200 combines the core and cuff of the previous embodiments into a single unit, which is fabricated of a single piece of ceramic material. The base of the abutment includes a collar 208, having a planar bottom side 210 which may fit flush against an implant, such as implant 202. The upper side of collar 208 has a lip 212 that extends around the periphery of collar 208. The coronal or top section 214 extends upwardly and is shaped similar to a tooth structure. A dental prosthesis, such as crown 204 in FIG. 7 fits upon lip 212 and atop upper section 214 of abutment 200.

Collar 208 is preferably gingival or pink-colored to match the gingival tissue surrounding implant 202 in a patient's mouth. By shading collar 208 with a pink or gingival-colored shade, the abutment will camouflage with surrounding dentition and gingival tissue in the patient's mouth if the gingival tissue in the patient's mouth should recede.

The abutments described herein may be used as is, or it may be necessary to alter and prepare the abutment to customize it to more precisely fit a patient. As shown in FIGS. 4 and 5, lip 212 forms the original cervical line of abutment 200. In preparing the abutment to better fit the patient's mouth, it may be necessary to move the cervical line to coincide with the cervical line in the patient's mouth, if gum tissue has receded. In order to adjust the cervical line, collar 208 may be fabricated of different colored layers of material. The inner core of collar 208 may be dentin-colored (to match the cervical area of the tooth) and the outer layer may be gingival-colored. The gingival-colored layer may vary in thickness from about 0.25 to about 1.00 mm. The technician may lower the cervical line as shown in FIGS. 4 and 5 by removing the gingival-colored layer covering the area 213 from the point of the original cervical line 212 to the new cervical line 215. By removing the gingival layer in area 215, the dentin-colored layer is revealed and the cervical line is moved from line 212 to line 213. The abutment is able to effectively camouflage with the patient's existing dentition and gingival tissue.

Upper or coronal section 214 is preferably divided into three regions, namely the cervical region 216, the central region 218 and the incisal region 220, which will have different shades or color to simulate the natural appearance of a tooth. These regions are mere approximations and vary from abutment to abutment, depending on the size, shape and dentition to which the abutment must correlate or match. Each region will have different requirements with regard to visual appearance. Thus, the appearance of lower or cervical region 216 of the abutment, which may vary from piece to piece, is preferably matched to the cervical region of the prosthesis and the cervical region of the surrounding dentition. The central region 218 of the abutment is preferably matched to the central region of the prosthesis and central region of the surrounding dentition. The incisal region 220 is preferably matched to the incisal region of the prosthesis and the incisal region of the surrounding dentition. Shade determination for the three coronal regions may be customized for the individual patient using one of the commercially available dental shade guides, for example, Chromoscop™ (Ivoclar Vivadent, Inc., Schaan, LI); Vitapan Classical™ (Vita-Lumin™ Vacuum Shade Guide) and Vitapan 3-D Master™ (Vident, Brea, Calif.); and Bioform™ and TruMatch™ (Dentsply International, Inc., Milford, Del.), or by using one of the commercially available intraoral spectrophotometers, for example, Easyshade (Vident, Brea, Calif.) and Shade Vision (X-Rite, Inc., Grand Rapids, Mich.). Accordingly, the natural tooth color of the abutment will enhance the natural appearance of the prosthesis.

Figure 8:
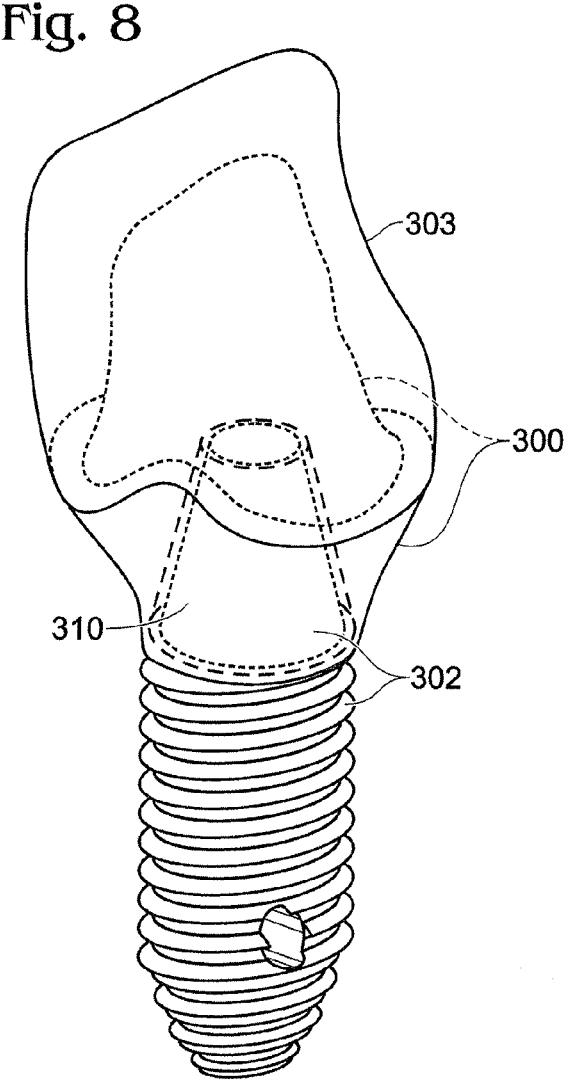
FIG. 8 is a perspective view of a dental implant system according to another embodiment of the present invention.
Figure 9:
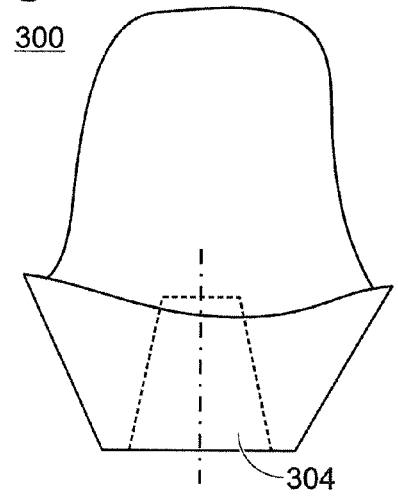
FIG. 9 is a perspective view of the facial side of the abutment in the implant system of FIG. 8.
Figure 10:
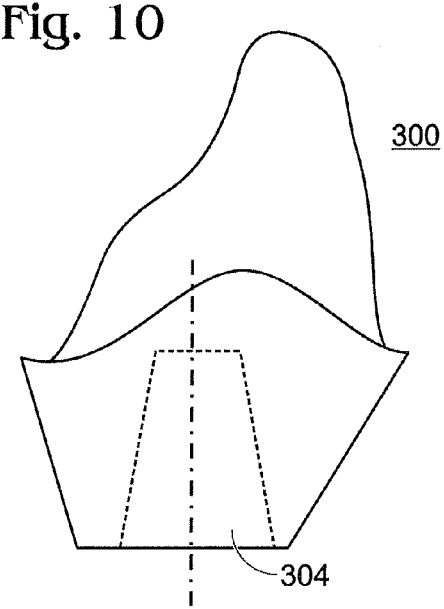
FIG. 10 is a perspective view of the facial side of the abutment in the implant system of FIG. 8.
Figure 11:
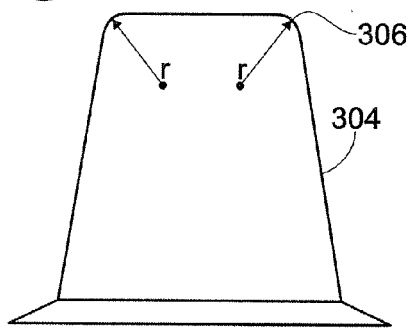
FIG. 11 is a perspective view of a bore in the abutment in FIGS. 9 and 10.
Figure 12:
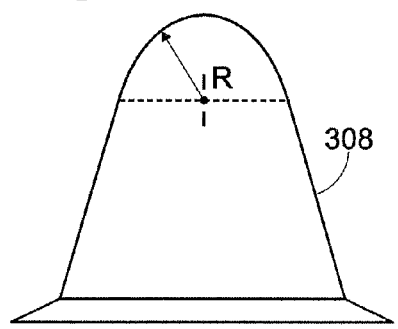
FIG. 12 is a perspective view of an alternative bore disposed in the abutment in FIGS. 9 and 10.

Reference is further made to FIGS. 8 through 10 which illustrate an abutment 300 showing an alternate form of attachment to an implant 302 and crown 303. Abutment 300 includes a bore 304 which fits flush with the conically-shaped top 306 of implant 302. Top 306 of implant 302 and bore 304 may vary in size, shape and/or design. It is preferable that bore 304 is tapered. FIG. 9 is a facial view of abutment 300 and FIG. 10 is a lateral view of abutment 300. FIGS. 11 and 12 show variations in the shape of bore 304. FIG. 11 shows a conical-shaped bore with beveled edges 306. FIG. 12 shows a semispherical-shaped bore 308. As with abutment 200, abutment 300 is a single-unit structure fabricated of a ceramic material.

Figure 13:
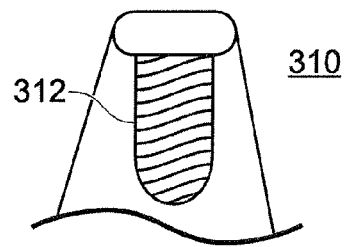
FIG. 13 is a close-up cut-away view of the top of the implant shown in FIG. 8.
Figure 14:
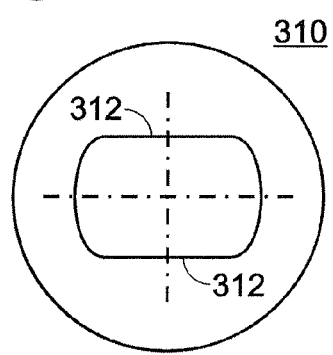
FIG. 14 is a top plan view of the implant in FIG. 13.

FIGS. 13 and 14 show a close-up view of an alternate embodiment of the top 310 of implant 302. Top 310 includes one or more chamfered sections 312 which prevent rotation of abutment 300 on implant 302 when stress is applied by the patient, for example, during chewing.

All the variations discussed above with respect to abutment 200 apply to abutment 300. The abutments herein may be customized in shape and color to enhance the natural effects provided by the dental prosthesis. By taking measurements of the site of desired tooth replacement and determining the type of tooth to be replaced, a model of an abutment can be selected from the inventory and/or customized to the proper shape and color to fit naturally with the patient's existing dentition.

As with abutment 104 having core section 120 and cuff 140, all configurations and anatomical variations discussed above are applicable to single-unit abutments 200 and 300, which combine the core and cuff into one monolithic unit.

The abutments may be shaded during manufacturing by coating oxide powder with one or more coloring substances to produce a colored powder, pressing the colored powder to produce a shaped body and sintering the compressed shaped body. Reference is made to commonly owned co-pending U.S. Patent Application Publication No. 20070292597 which discloses a method of making zirconia multi-colored blanks and products thereof, U.S. Pat. No. 6,379,593, which discloses a method of making a multi-colored ceramic body, and U.S. Pat. No. 4,970,032, which discloses layered blanks for milling dental materials, all of which are hereby incorporated by reference in their entirety. It is also possible to fabricate partially or fully sintered blanks, which can be further milled into the desired abutment shape.

Alternatively, the abutment may be fabricated of a ceramic material which has been partially or fully sintered and thereafter shaded by staining the partially or fully sintered abutment with stains to match the prosthesis, surrounding tooth surface and surrounding gingival tissue.

It is preferable that the ceramic material is a high strength ceramic material such as zirconia, alumina, and mixtures thereof whereby the flexural strength is greater than about 1000 MPa, more preferably greater than about 1500 MPa, and most preferably greater than about 2000 MPa. Some applicable materials are known in the art as yttria or ceria-stabilized tetragonal zirconia (Y-TZP and Ce-TZP), zirconia toughened alumina (ZTA), alumina-toughened zirconia (ATZ), mixtures thereof, composites thereof and functionally graded composites thereof. The flexural strength of these materials customarily exceeds 1000 MPa with better ones exceeding 1500 MPa and even 2000 MPa. Examples of materials useful herein include, but are not limited to, ZirCAD™ blocks from Ivoclar Vivadent, nanoZir™ zirconia from Hint-ELs and Ziraldent™ material from Metoxit AG.

In addition to the abutment being anatomically shaded as described above to simulate natural dentition and to further match the surrounding dentition and gingival tissue in a patient's mouth, the abutment may also be anatomically shaped to match the shape of the surrounding dentition, gingival tissue and prosthesis which is positioned thereon. It is most preferable that abutment 200 has a shape that is near the net tooth shape of the prosthesis to which it will be attached and a shade that is anatomically shaded to match natural dentition such that the color and translucency distribution characteristics simulate natural dentition. The anatomically shaded multicolor abutment mimics the color and translucency distribution in natural teeth in such a way that a crown, positioned on the abutment, will require no or very little veneering porcelain to mimic the replaced tooth. The near net shape and shade of the abutment obviates the need to use a thick crown over the abutment, improving the overall strength and structural integrity of the implant system without compromising aesthetics. Since more strength is provided by the abutment, less strength is needed in the crown or veneering layer (porcelain or composite), which sits atop the abutment. The esthetic contribution of the veneering layer becomes, if not less important, at least more consistent and predictable. As the abutment gets closer to the net shape and becomes more naturally shaded, it obviates the need for a restoration on top, and it becomes the restoration itself. In addition to the materials mentioned above, the net shaped abutment may be fabricated of lithium disilicate with flexural strength exceeding 600 MPa, as disclosed in commonly owned, copending U.S. Patent Application Publication No. 20070042889, which is hereby incorporated by reference in its entirety.

In selecting the correct shades for the abutment, the color components, hue, chroma and value, are evaluated. Hue is the dimension of color that enables us to distinguish one family of color from another; chroma defines the relative intensity of a particular color, i.e., the more intense a color is, the higher its chroma level; and value describes the relative whiteness or blackness of a particular color, i.e., the brighter the color, the higher its value. In addition to these components, characteristics such as opacity, fluorescence, and translucency may also be considered during the determination of the correct shades for the abutment.

A finished dental restoration should match the color of the patient's teeth, i.e., it should be "tooth colored". The colors of human teeth appear to range from a light, almost white-tan to a light brown, and occupy a very specific color space. This color space can be described by the commonly used CIE (Commission Internationale de l'Eclariage) L*, a*, b* conventions, which represents colors in a three-dimensional Cartesian coordinate system. L*, or "value", is a measure of luminance or lightness, and is represented on the vertical axis (black is 0 and white is 100). The a*, b* coordinates, are a measure of chromaticity and are represented on the horizontal coordinates, with positive a* representing red and negative a* representing green, and positive b* representing yellow and negative b* representing blue. U.S. Pat. No. 6,030,209, which is incorporated herein by reference, presents the CIE L*, a*, b* color coordinates of tooth colors represented by the Vita Lumen® shade guide system manufactured by Vita Zahnfabrik (i.e., it presents the color space of tooth colors). Herein, "tooth color" is taken to mean CIE L*, a*, b* color coordinates that fall within, or very close to, this color space.

In the fabrication of the abutment herein, the ranges of the L*a*b* values are set forth in Table 1 below along with the amount of opacity preferred.

TABLE 1

| Range | L* | a* | b* | Opacity (CR)% |
|---|---|---|---|---|
| Min | 27.00 | −17.00 | −29.00 | 5.00 |
| Max | 96.00 | +28.00 | +52.00 | 99.00 |

The values will vary in the abutment, depending on the area to be shaded. Table 2 sets forth ranges for the gingival, cervical, central (matched to dentin) and incisal regions.

TABLE 2

| Abutment Areas | L* | a* | b* |
|---|---|---|---|
| Gingival | 40-75 | 12-25 | 6-20 |
| Cervical | 70-90 | −2-+10 | 12-36 |
| Dentin | 60-80 | −3-+10 | 12-36 |
| Incisal | 50-75 | −1 + 10 | −1 + 30 |

The single-unit abutment is facile and effective way to provide a natural-looking prosthesis. The gingival-colored base section of the abutment is able to camouflage with the surrounding gingival tissue and the coronal section enhances the natural look of the prosthesis.

EXAMPLE

Adequate alveolar bone must first be present at an edentulous site in order to properly treat a patient with a dental implant. After the secure placement of the dental implant in the patient's jawbone, an appropriate abutment type is selected that will provide support for the final restoration. Where the final restoration being considered is an all-ceramic restoration, selection of an implant abutment according to the present invention, that is color-shaded similar to natural teeth is suggested, as opposed to a metallic abutment which may shadow through the ceramic prosthesis and affect the color of the all-ceramic restoration. An impression and shade is taken using one of the known shade guide systems and sent to the laboratory for fabrication of the final restoration. The color of the abutment is matched to the chosen color for the restoration. The final restoration is then fit within the patient's mouth and permanently mounted.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A dental implant abutment comprising:
a monolithic single unit structure having a basal end for anchoring to an implant and a coronal end for supporting a dental prosthesis, wherein the basal end and coronal end meet at a cervical line;
wherein the monolithic single unit structure is fabricated of a ceramic material;
wherein the monolithic single unit structure is multicolored throughout and anatomically shaped and shaded to match the color and contour of the dental prosthesis, the surrounding dentition and the surrounding gingival tissue;
wherein the basal end comprises a collar having a lower side and an upper side, the upper side of the collar forming the cervical line, the collar further comprising a core and an outer layer of material overlaying the core, wherein the core is a dentin color and wherein the outer layer is a gingival color, and wherein the cervical line may be lowered by removing the outer layer of material; wherein the ceramic material has a flexural strength exceeding 1000 MPa.

2. The dental implant abutment of claim 1 wherein the multicolored single unit structure varies in shade, translucency, opacity, opalescence, and fluorescence from the basal end to the coronal end.

3. The dental implant abutment of claim 2 wherein the basal end is gingival pink-colored, the coronal end is incisal-colored and the area in between the basal and coronal ends is dentin colored.

4. The dental implant abutment of claim 3 wherein the dentin-colored area includes a cervical-colored area where the basal end meets the coronal end.

5. The implant abutment of claim 2 wherein the shade is measured by CIE L*, a*, and b* color coordinates and wherein the CIE L*, a*, and b* color coordinates are within the CIE L*, a*, and b* color space region associated with tooth colors and translucencies.

6. The dental implant abutment of claim 5 wherein value L* ranges from about 27 to about 96, value a* ranges from about −17 to about +28, value b* ranges from about −29 to about +52 and the contrast ratio (CR) ranges from about 5 to about 99%.

7. The dental implant abutment of claim 1 wherein the ceramic material comprises zirconia, alumina, a composite thereof or a mixture thereof.

8. The dental implant of claim 7 wherein the composite comprises functionally graded composites.

9. The dental implant of claim 7 wherein the composite or mixture comprises zirconia-toughened alumina or alumina-toughened zirconia.

10. The dental implant abutment of claim 1 wherein the ceramic material has a flexural strength exceeding 1500 MPa.

11. The dental implant abutment of claim 1 wherein the ceramic material has a flexural strength exceeding 2000 MPa.

12. The dental implant abutment of claim 1 wherein the outer layer of material has a thickness in the range from about 0.25 to about 1.00 mm.

13. The dental implant abutment of claim 1 wherein the location of the cervical line changes after the abutment is prepared for placement on an implant.

14. The dental implant abutment of claim 13 wherein the abutment is prepared using hand-held instruments and procedures, partially automated instruments and procedures, or fully automated instruments and procedures.

15. A dental implant restoration system comprising:
an implant;
an abutment fixed to an implant; and
a dental prosthesis disposed atop the abutment;
wherein the abutment comprises a monolithic, single-unit structure having a basal end for anchoring to an implant and a coronal end for supporting a dental prosthesis, wherein the basal end and coronal end meet at a cervical line;
wherein the monolithic single-unit structure is fabricated of a ceramic material;
wherein the monolithic single-unit structure is multicolored throughout and anatomically shaped and shaded to match the color and contour of the dental prosthesis, the surrounding dentition and the surrounding gingival tissue;
wherein the basal end comprises a collar having a lower side and an upper side, the upper side of the collar forming the cervical line, the collar further comprising a core and an outer layer of material overlaying the core, wherein the core is a dentin color and wherein the outer layer is a gingival color, and wherein the cervical line may be lowered by removing the outer layer of material; wherein the ceramic material has a flexural strength exceeding 1000 MPa.

16. The dental implant restoration system of claim 15 wherein the abutment is attached to the implant externally by a screw or internally by a bore contained in the abutment.

17. The dental implant restoration system of claim 15 wherein the implant comprises a male connection component and the abutment comprises a female connection component to connect to one another.

18. The dental implant restoration system of claim 15 wherein the implant comprises a female connection component and the abutment comprises a male connection component to connect to one another.

19. The dental implant restoration system of claim 15 wherein the basal end is gingival pink-colored, the coronal end is incisal-colored and the area in between the basal and coronal ends is dentin colored.

20. The dental implant restoration system of claim 15 wherein the ceramic material has a flexural strength exceeding 1500 MPa.

21. The dental implant restoration system of claim 15 wherein the ceramic material has a flexural strength exceeding 2000 MPa.

22. The dental implant restoration system of claim 15 wherein the outer layer of material has a thickness in the range from about 0.25 to about 1.00 mm.

23. The dental implant restoration system of claim 15 wherein the location of the cervical line changes after the abutment is prepared for placement on an implant.

24. The implant restoration system of claim 23 wherein the abutment is prepared using hand-held instruments and procedures, partially automated instruments and procedures, or fully automated instruments and procedures.

25. The dental implant restoration system of claim 15 wherein the dental prosthesis comprises dental ceramic, porcelain, composite or hybrid material.

26. The dental implant restoration system of claim 25 wherein the dental ceramic, porcelain, composite or hybrid material is fabricated using hand-held instruments and procedures, partially automated instruments and procedures, or fully automated instruments and procedures.

27. The dental implant restoration system of claim 26 wherein the partially or fully automated instruments and procedures comprises CAD/CAM, Rapid-Prototyping, plasma or flame deposition, electroforming, spraying or dipping.

28. A dental implant restoration system comprising:
an implant; and
an anatomically shaped and shaded abutment fixed to the implant;
wherein the anatomically shaped and shaded abutment comprises a near net-shape monolithic, single-unit structure having a basal end for anchoring to an implant and a coronal end approximating the shape of a dental prosthesis, wherein the basal end and coronal end meet at a cervical line;
wherein the monolithic single-unit structure is fabricated of a ceramic material;
wherein the monolithic single-unit structure is multicolored throughout to match the color of the dental prosthesis, the surrounding dentition and the surrounding gingival tissue;
wherein the basal end comprises a collar having a lower side and an upper side, the upper side of the collar forming the cervical line, the collar further comprising a core and an outer layer of material overlaying the core, wherein the core is a dentin color and wherein the outer layer is a gingival color, and wherein the cervical line may be lowered by removing the outer layer of material; wherein the ceramic material has a flexural strength exceeding 1000 MPa.

29. The dental implant restoration system of claim 28 wherein the outer layer of material has a thickness in the range from about 0.25 to about 1.00 mm.

30. The dental implant restoration system of claim 28 wherein the location of the cervical line changes after the abutment is prepared for placement on an implant.

31. The implant restoration system of claim 30 wherein the abutment is prepared and/or finished using hand-held instruments and procedures, partially automated instruments and procedures, or fully automated instruments and procedures.

32. The dental implant restoration system of claim 28 further comprising an aesthetic layer.

33. The dental implant restoration system of claim 31 wherein the finishing the abutment comprises cutting-back and layering.

34. The dental implant restoration system of claim 31 wherein finishing the abutment comprises staining and glazing.

35. The dental implant restoration system of claim 28 wherein the abutment requires no aesthetic layer prior to placement onto the dental implant in the patient's mouth.

36. The dental implant restoration system of claim 28 wherein the ceramic material comprises zirconia, alumina, lithium disilicate, a composite thereof or a mixture thereof.

37. The dental implant restoration system of claim 15 wherein the dental prosthesis is disposed atop the abutment by pressing or layering a veneering material directly onto the abutment.

38. The dental implant restoration system of claim 32 wherein the aesthetic layer is a veneering material comprising dental ceramic, porcelain, composite or hybrid material.

39. The dental implant restoration system of claim 38 wherein the dental ceramic, porcelain, composite or hybrid material is fabricated using hand-held instruments and procedures, partially automated instruments and procedures, or fully automated instruments and procedures.

40. The dental implant restoration system of claim 39 wherein the partially or fully automated instruments and procedures comprises CAD/CAM, Rapid-Prototyping, plasma or flame deposition, electroforming, spraying or dipping.

* * * * *